US008221837B2

(12) United States Patent
Meiere

(10) Patent No.: US 8,221,837 B2
(45) Date of Patent: Jul. 17, 2012

(54) ORGANOMETALLIC COMPOUNDS AND PROCESSES FOR PREPARATION THEREOF

(75) Inventor: Scott Houston Meiere, Williamsville, NY (US)

(73) Assignee: Praxair Technology, Inc., Danbury, CT (US)

( * ) Notice: Subject to any disclaimer, the term of this patent is extended or adjusted under 35 U.S.C. 154(b) by 0 days.

(21) Appl. No.: 13/101,482

(22) Filed: May 5, 2011

(65) Prior Publication Data

US 2011/0206845 A1 Aug. 25, 2011

Related U.S. Application Data

(62) Division of application No. 11/216,043, filed on Sep. 1, 2005, now Pat. No. 7,619,093.

(51) Int. Cl.
 *C23C 16/18* (2006.01)
 *C07F 15/00* (2006.01)
(52) U.S. Cl. .................... 427/255.21; 548/402
(58) Field of Classification Search ............. 427/255.21; 548/402
See application file for complete search history.

(56) References Cited

U.S. PATENT DOCUMENTS

| 6,884,901 B2 | 4/2005 | Thompson et al. |
| 2007/0054487 A1 | 3/2007 | Ma et al. |
| 2007/0077750 A1 | 4/2007 | Ma et al. |
| 2011/0135838 A1* | 6/2011 | Lei et al. .................. 427/535 |

FOREIGN PATENT DOCUMENTS

| JP | 59108003 A | 6/1984 |
| JP | 61126555 | 6/1986 |
| JP | 2001122887 | 5/2001 |
| JP | 2002255918 | 9/2002 |
| JP | 2003342286 | 12/2003 |
| JP | 2004107391 | 4/2004 |
| JP | 2005154362 | 6/2005 |
| JP | 2006056849 | 3/2006 |

OTHER PUBLICATIONS

Efraty et al. Chemistry of Some (η5-Pyrrolyl)- and (η1-N-pPyrrolyl)iron Complexes. Inorganic Chemistry, 1982, 21(3), pp. 868-873.
Fukuda et al. Enantioselective Synthesis of Planar Chiral Azaferrocenes via Chiral Ligand-Mediated Ring- and Lateral-Lithiations. Tetrahedron Letters, 2003, 44(40), pp. 7503-7506.
Hansen et al. Pentamethylated and Pentaphenylated Azeferro- and Azaruthenocenes: Simple and General Methodology for the Preparation of Enatiopure Derivatives. Journal of Organic Chemistry, 2003, 68(4), pp. 1266-1274.
Joshi et al. Metal Complexes of Heterocycles I. The Preparation of Pyrrolyl Manganese and Iron Derivatives. Journal of Organometallic Chemistry. 1964, 1(6), pp. 471-475.
Kowalski et al. Lithiation of 2,5-dimethylazaferrocene. Journal of Organometallic Chemistry, 2004, 689(6), pp. 1046-1049.
Kuhn et al. 2,2', 5,5'-Tetra-tert-butyl-3,3'-bis(trimethylsilyl)-1,1'-diazacobaltocen. Zeitschrift fuer Naturforschung, B: Chemical Sciences, 1999, 54(3), pp. 424-426.
Kuhn et al. Heterocycles as Coordinating Ligands Part VII, New Pyrrolyl Iron Complexes. Inorganica Chimica Acta, 1990, 170(2), pp. 155-156.
Kuhn et al. Heterocycles as ligands. XIX. The electronic structure of 1,1'-diazametallocenes and the synthesis and crystal structure of 1,2', 5,5'-tetra-tert-butyl-1,1'-diazanickelocene. Journal of Organometallic Chemistry, 1993, 456(1), pp. 97-106.
Kuhn et al. Synthese and Charakterisierung von 2,3,4,5-Tetramethyl-1-azaferrocen. Chemische Berichte, 1989, 122(10), pp. 1891-1896.
Kvietok et al. Synthesis and Reactions of Ruthenium Pyrrole Complexes. Preprints—American Chemical Society, Division of Petroleum Chemistry, 1993, 38(3), pp. 671-673.
Pauson et al. Metal Complexes of Heterocycles III*, Acetylpyrrolyl and Indolyl Complexes. Journal of Organometallic Chemistry, 1967, 7(2), pp. 325-328.
Perera et al. η5-Imidazolato Complexes of Ruthenium. Organometallics, 2000, 19(25), pp. 5263-5265.
Pyshnograeva et al. Metallatiojn of Azaferrocene. Journal of Organometallic Chemistry, 1983, 251(2), pp. C41-C43.
Ruble et al. Chiral π-Complexes of Heterocycles with Transition Metals: A Versatile New Family of Nucleophilic Catalysts. Journal of Organic Chemistry, 1996 61(21), pp. 7230-7231.
Schumann et al. Organometallic Compounds of the Lanthanides, CIII. Mixed Sandwich Complexes of the 4f Elements: Synthesis and Crystal Structure of (η8-cyclooctatetraenyl) (η5-2,5-di-ter.-butylpyrrolyl) samarium, -thulium, and -lutetium. Journal of Organometallic Chemistry, 1996, 507 (1-2), pp. 287-289.
DuBois et al. "The activation of $\eta^5$-pyrrole complexes toward nucleophilic attack", *Coordination Chemistry Reviews* 174 (1998) 191-205.
DuBois et al., Nucleophilic Substitution of $\eta^5$-Pyrrolyl Ligands in Ruthenium (II) Complexes, *Organometallics* 1997, 16, 2325-2334.
Garrett et al., "Nucleophilic Catalysts with pi-Bound Nitrogen Heterocycles: Synthesis of the First Ruthenium Catalysts and Comparison of the Reactivity and the Enantioselectivity of Ruthenium and Iron Complexes" *Journal of the American Chemical Society*, 1998, vol. 120, pp. 7479-7483.
Kelly et al. "Azaruthenocenes: Preparation of [n5-C4Me4N)Ru(n5-C5Me5)] and [n5-C4Me4N)2Ru], the First Ruthenium Metallocenes Incorporating n5-Pyrrolyl Ligands" *Organometallics*, 1992, vol. 11, pp. 4348-4350.
Lim et al., "Synthesis and Characterization of Volatile, Thermally Stable, Reactive Transition Metal Amidinates", *Inorganic Chem, Preprint*, 2003.

(Continued)

*Primary Examiner* — Joseph Kosack
(74) *Attorney, Agent, or Firm* — Nilay S. Dalal

(57) ABSTRACT

This invention relates to organometallic compounds represented by the formula LML' wherein M is a metal or metalloid, L is a substituted or unsubstituted cyclopentadienyl group or cyclopentadienyl-like group, a substituted or unsubstituted pentadienyl group or pentadienyl-like group, or a substituted or unsubstituted pyrrolyl group or pyrrolyl-like group, and L' is a substituted or unsubstituted pyrrolyl group or pyrrolyl-like group, a process for producing the organometallic compounds, and a method for producing a film or coating from the organometallic compounds. The organometallic compounds are useful in semiconductor applications as chemical vapor or atomic layer deposition precursors for film depositions.

6 Claims, No Drawings

OTHER PUBLICATIONS

McComas et al. Neutral Ru($\eta^5$-pyrrole) Complexes. Synthesis and Structure of Diazaruthenocenes and Ru(1-3:5. 6-$\eta^5$-$C_8^H$11) ($\eta^5$-pyrrole) Complexes, *Organometallics 2000*, 19, 2853-2857.

Perera et al. "Ruthenium Complexes Bearing n5-Pyrazolato Ligands" *J. Am. Chem. Soc.* 1999, 121, 4536-4537.

Platinum Metals Rev. "Potential Uses of Ruthenium-Molybdenum and Ruthenium-Tungsten Alloys" 1973, 17 (4), p. 143.

Vendemiata et al. "Paramagnetic Bis(amidinate) Iron (II) Complexes and their Diamagnetic Dicarbonyl Derivatives" *Eur. J. Inorg. Chem.* 2001, 707-711.

\* cited by examiner

ORGANOMETALLIC COMPOUNDS AND PROCESSES FOR PREPARATION THEREOF

RELATED APPLICATIONS

This application is a divisional of prior U.S. application Ser. No. 11/216,043, filed Sep. 1, 2005 now U.S. Pat. No. 7,619,093, the entire contents of which is incorporated herein by reference in its entirety. This application is related to Divisional application Ser. No. 12/564,990, filed Sep. 23, 2009, now allowed.

FIELD OF THE INVENTION

This invention relates to organometallic compounds represented by the formula LML' wherein M is a metal or metalloid, L is a substituted or unsubstituted cyclopentadienyl group or cyclopentadienyl-like group, a substituted or unsubstituted pentadienyl group or pentadienyl-like group, or a substituted or unsubstituted pyrrolyl group or pyrrolyl-like group, and L' is a substituted or unsubstituted pyrrolyl group or pyrrolyl-like group, a process for producing the organometallic compounds, and a method for producing a film or coating from the organometallic compounds.

BACKGROUND OF THE INVENTION

Chemical vapor deposition methods are employed to form films of material on substrates such as wafers or other surfaces during the manufacture or processing of semiconductors. In chemical vapor deposition, a chemical vapor deposition precursor, also known as a chemical vapor deposition chemical compound, is decomposed thermally, chemically, photochemically or by plasma activation, to form a thin film having a desired composition. For instance, a vapor phase chemical vapor deposition precursor can be contacted with a substrate that is heated to a temperature higher than the decomposition temperature of the precursor, to form a metal or metal oxide film on the substrate. Preferably, chemical vapor deposition precursors are volatile, heat decomposable and capable of producing uniform films under chemical vapor deposition conditions.

The semiconductor industry is currently considering the use of thin films of ruthenium metal for a variety of applications. Many organometallic complexes have been evaluated as potential precursors for the formation of these thin films. These include, for example, carbonyl complexes such as $Ru_3(CO)_{12}$, diene complexes such as $Ru(\eta^3\text{-}C_6H_8)(CO)_3$, $Ru(\eta^3\text{-}C_6H_8)(\eta^6\text{-}C_6H_6)$, beta-diketonates such as $Ru(DPM)_3$, $Ru(OD)_3$ and ruthenocenes such as $RuCp_2$, $Ru(EtCp)_2$.

Both the carbonyl and diene complexes tend to exhibit low thermal stabilities which complicates their processing. While the beta-diketonates are thermally stable at moderate temperatures, their low vapor pressures married with their solid state at room temperature make it difficult to achieve high growth rates during film deposition.

Ruthenocenes have received considerable attention as precursors for Ru thin film deposition. While ruthenocene is a solid, the functionalization of the two cyclopentadienyl ligands with ethyl substituents yields a liquid precursor that shares the chemical characteristics of the parent ruthenocene. Unfortunately, depositions with this precursor have generally exhibited long incubation times and poor nucleation densities.

U.S. Pat. No. 6,605,735 B2 discloses half-sandwich organometallic ruthenium compounds that have a cyclopentadienyl and pentadienyl group bonded to ruthenium. The cyclopentadienyl group can be mono-substituted or unsubstituted. The pentadienyl group can be mono-, di- or tri-substituted or unsubstituted. Certain substitution patterns are specifically excluded. It is stated in the patent that the inventors conducted extensive studies and found that the decomposition temperature of a ruthenocene can be lowered by substituting one of the cyclopentadienyl rings by linear pentadienyl. By introducing a single lower alkyl group into the cyclopentadienyl ring, it is stated in the patent that the half-sandwich organometallic ruthenium compounds have been found to be liquid at room temperature and exhibit favorable vaporization and decomposition properties. These compounds are used for producing a ruthenium-containing thin film by chemical vapor deposition.

In developing methods for forming thin films by chemical vapor deposition or atomic layer deposition methods, a need continues to exist for precursors that preferably are liquid at room temperature, have adequate vapor pressure, have appropriate thermal stability (i.e., for chemical vapor deposition will decompose on the heated substrate but not during delivery, and for atomic layer deposition will not decompose thermally but will react when exposed to co-reactant), can form uniform films, and will leave behind very little, if any, undesired impurities (e.g., halides, carbon, etc.). Therefore, a need continues to exist for developing new compounds and for exploring their potential as chemical vapor or atomic layer deposition precursors for film depositions. It would therefore be desirable in the art to provide a precursor that possesses some, or preferably all, of the above characteristics.

SUMMARY OF THE INVENTION

This invention relates in part to organometallic compounds selected from the following:

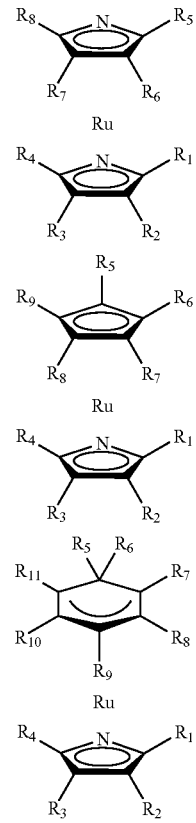

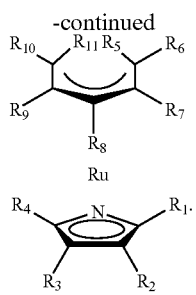

wherein $R_1$, $R_2$, $R_3$, $R_4$, $R_5$, $R_6$, $R_7$, $R_8$, $R_9$, $R_{10}$ and $R_{11}$ are the same or different and each represents hydrogen, a halogen atom, an acyl group having from 1 to about 12 carbon atoms, an alkoxy group having from 1 to about 12 carbon atoms, an alkoxycarbonyl group having from 1 to about 12 carbon atoms, an alkyl group having from 1 to about 12 carbon atoms, an amine group having from 1 to about 12 carbon atoms or a silyl group having from 0 to about 12 carbon atoms.

More generally, this invention relates in part to organometallic compounds represented by the formula LML' wherein M is a metal or metalloid, L is a substituted or unsubstituted cyclopentadienyl group, a substituted or unsubstituted cyclopentadienyl-like group, a substituted or unsubstituted pentadienyl group, a substituted or unsubstituted pentadienyl-like group, a substituted or unsubstituted pyrrolyl group or a substituted or unsubstituted pyrrolyl-like group, and L' is a substituted or unsubstituted pyrrolyl group or a substituted or unsubstituted pyrrolyl-like group.

This invention also relates in part to a process for the production of an organometallic compound represented by the formula LML' wherein M is a metal or metalloid, L is a substituted or unsubstituted cyclopentadienyl group, a substituted or unsubstituted cyclopentadienyl-like group, a substituted or unsubstituted pentadienyl group, a substituted or unsubstituted pentadienyl-like group, a substituted or unsubstituted pyrrolyl group or a substituted or unsubstituted pyrrolyl-like group, and L' is a substituted or unsubstituted pyrrolyl group or a substituted or unsubstituted pyrrolyl-like group, which process comprises (i) reacting a metal source compound selected from a substituted or unsubstituted cyclopentadienyl halide metal compound, a substituted or unsubstituted cyclopentadienyl-like halide metal compound, a substituted or unsubstituted pentadienyl halide metal compound, a substituted or unsubstituted pentadienyl-like halide metal compound, a substituted or unsubstituted pyrrolyl halide metal compound or a substituted or unsubstituted pyrrolyl-like halide metal compound, with a base material in the presence of a solvent and under reaction conditions sufficient to produce a reaction mixture comprising said organometallic compound, and (ii) separating said organometallic compound from said reaction mixture. The organometallic compound yield resulting from the process of this invention can be 60% or greater, preferably 75% or greater, and more preferably 90% or greater.

This invention further relates in part to a method for producing a film, coating or powder by decomposing an organometallic compound represented by the formula LML' wherein M is a metal or metalloid, L is a substituted or unsubstituted cyclopentadienyl group, a substituted or unsubstituted cyclopentadienyl-like group, a substituted or unsubstituted pentadienyl group, a substituted or unsubstituted pentadienyl-like group, a substituted or unsubstituted pyrrolyl group or a substituted or unsubstituted pyrrolyl-like group, and L' is a substituted or unsubstituted pyrrolyl group or a substituted or unsubstituted pyrrolyl-like group, thereby producing the film, coating or powder. Typically, the decomposing of said organometallic compound is thermal, chemical, photochemical or plasma-activated. Film deposition is preferably self-limiting and conducted in the presence of at least one reactive gas such as hydrogen.

This invention also relates in part to organometallic mixtures comprising (i) a first organometallic compound represented by the formula LML' wherein M is a metal or metalloid, L is a substituted or unsubstituted cyclopentadienyl group, a substituted or unsubstituted cyclopentadienyl-like group, a substituted or unsubstituted pentadienyl group, a substituted or unsubstituted pentadienyl-like group, a substituted or unsubstituted pyrrolyl group or a substituted or unsubstituted pyrrolyl-like group, and L' is a substituted or unsubstituted pyrrolyl group or a substituted or unsubstituted pyrrolyl-like group, and (ii) one or more different organometallic compounds (e.g., a hafnium-containing, tantalum-containing or molybdenum-containing organometallic precursor compound).

This invention relates in particular to depositions involving pyrrolide-based ruthenium precursors. These precursors can provide advantages over the other known precursors, especially when utilized in tandem with other 'next-generation' materials (e.g., hafnium, tantalum and molybdenum). These ruthenium-containing materials can be used for a variety of purposes such as dielectrics, barriers, and electrodes, and in many cases show improved properties (thermal stability, desired morphology, less diffusion, lower leakage, less charge trapping, and the like) than the non-ruthenium containing films.

The invention has several advantages. For example, the method of the invention is useful in generating organometallic compounds that have varied chemical structures and physical properties. Films generated from the organometallic compounds can be deposited with a short incubation time, and the films deposited from the organometallic compounds exhibit good smoothness. These pyrrolyl-containing ruthenium precursors may be deposited by atomic layer deposition employing a hydrogen reduction pathway in a self-limiting manner, thereby enabling use of ruthenium as a barrier/adhesion layer in conjunction with tantalum nitride in BEOL (back end of line) liner applications. Such pyrrolyl-containing ruthenium precursors deposited in a self-limiting manner by atomic layer deposition may enable conformal film growth over high aspect ratio trench architectures in a reducing environment.

This invention relates in particular to chemical vapor deposition and atomic layer deposition precursors for next generation devices, specifically pyrrolyl-containing ruthenium precursors that are liquid at room temperature, i.e., 20° C. The pyrrolyl-containing ruthenium compounds are preferably hydrogen reducible and deposit in a self-limiting manner.

DETAILED DESCRIPTION OF THE INVENTION

As indicated above, this invention relates in part to organometallic compounds represented by the formula LML' wherein M is a metal or metalloid, L is a substituted or unsubstituted cyclopentadienyl group, a substituted or unsubstituted cyclopentadienyl-like group, a substituted or unsubstituted pentadienyl group, a substituted or unsubstituted pentadienyl-like group, a substituted or unsubstituted pyrrolyl group or a substituted or unsubstituted pyrrolyl-like group, and L' is a substituted or unsubstituted pyrrolyl group or a substituted or unsubstituted pyrrolyl-like group.

In a preferred embodiment, this invention relates in part to organometallic ruthenium compounds selected from

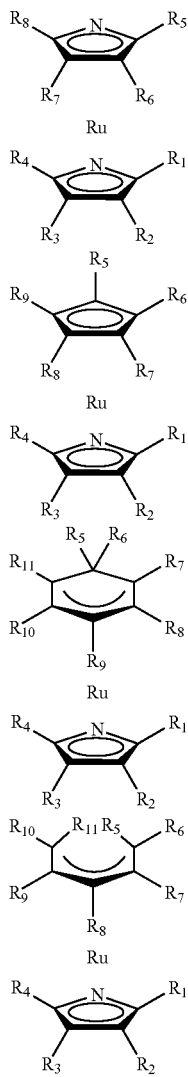

wherein $R_1$, $R_2$, $R_3$, $R_4$, $R_5$, $R_6$, $R_7$, $R_8$, $R_9$, $R_{10}$ and $R_{11}$ are the same or different and each represents hydrogen, a halogen atom, an acyl group having from 1 to about 12 carbon atoms, an alkoxy group having from 1 to about 12 carbon atoms, an alkoxycarbonyl group having from 1 to about 12 carbon atoms, an alkyl group having from 1 to about 12 carbon atoms, an amine group having from 1 to about 12 carbon atoms or a silyl group having from 0 to about 12 carbon atoms.

Other organometallic compounds within the scope of this invention can be represented by the formula $(L)_2M'L'$ or $LM'(L')_2$ wherein M' is a lanthanide, L is the same or different and is a substituted or unsubstituted cyclopentadienyl group, a substituted or unsubstituted cyclopentadienyl-like group, a substituted or unsubstituted pentadienyl group, a substituted or unsubstituted pentadienyl-like group, a substituted or unsubstituted pyrrolyl group or a substituted or unsubstituted pyrrolyl-like group, and L' is the same or different and is a substituted or unsubstituted pyrrolyl group or a substituted or unsubstituted pyrrolyl-like group.

Illustrative substituted cyclopentadienyl-like moieties include cyclo-olefin e.g., cyclohexadienyl, cycloheptadienyl, cyclooctadienyl rings, heterocyclic rings, aromatic rings, such as substituted benzenyl, and others, as known in the art. Illustrative substituted or unsubstituted pentadienyl-like groups include linear olefinic groups, e.g., hexadienyl, heptadienyl, octadienyl, and others, as known in the art. Illustrative substituted or unsubstituted pyrrolyl-like groups include pyrrolinyl, pyrazolyl, thiazolyl, oxazolyl, imidazolyl, carbazolyl, triazolyl, indolyl and purinyl.

Permissible substituents of the substituted cyclopentadienyl and cyclopentadienyl-like groups (L), the substituted pentadienyl and pentadienyl-like groups (L) and also the substituted pyrrolyl and pyrrolyl-like groups (L and L') include halogen atoms, acyl groups having from 1 to about 12 carbon atoms, alkoxy groups having from 1 to about 12 carbon atoms, alkoxycarbonyl groups having from 1 to about 12 carbon atoms, alkyl groups having from 1 to about 12 carbon atoms, amine groups having from 1 to about 12 carbon atoms or silyl groups having from 0 to about 12 carbon atoms.

Illustrative halogen atoms that may be used in $R_1$, $R_2$, $R_3$, $R_4$, $R_5$, $R_6$, $R_7$, $R_8$, $R_9$, $R_{10}$ and $R_{11}$ include, for example, fluorine, chlorine, bromine and iodine. Preferred halogen atoms include chlorine and fluorine.

Illustrative acyl groups that may be used in $R_1$, $R_2$, $R_3$, $R_4$, $R_5$, $R_6$, $R_7$, $R_8$, $R_9$, $R_{10}$ and $R_{11}$ include, for example, formyl, acetyl, propionyl, butyryl, isobutyryl, valeryl, 1-methylpropylcarbonyl, isovaleryl, pentylcarbonyl, 1-methylbutylcarbonyl, 2-methylbutylcarbonyl, 3-methylbutylcarbonyl, 1-ethylpropylcarbonyl, 2-ethylpropylcarbonyl, and the like. Preferred acyl groups include formyl, acetyl and propionyl.

Illustrative alkoxy groups that may be used in $R_1$, $R_2$, $R_3$, $R_4$, $R_5$, $R_6$, $R_7$, $R_8$, $R_9$, $R_{10}$ and $R_{11}$ include, for example, methoxy, ethoxy, n-propoxy, isopropoxy, n-butoxy, isobutoxy, sec-butoxy, tert-butoxy, pentyloxy, 1-methylbutyloxy, 2-methylbutyloxy, 3-methylbutyloxy, 1,2-dimethylpropyloxy, hexyloxy, 1-methylpentyloxy, 1-ethylpropyloxy, 2-methylpentyloxy, 3-methylpentyloxy, 4-methylpentyloxy, 1,2-dimethylbutyloxy, 1,3-dimethylbutyloxy, 2,3-dimethylbutyloxy, 1,1-dimethylbutyloxy, 2,2-dimethylbutyloxy, 3,3-dimethylbutyloxy, and the like. Preferred alkoxy groups include methoxy, ethoxy and propoxy.

Illustrative alkoxycarbonyl groups that may be used in $R_1$, $R_2$, $R_3$, $R_4$, $R_5$, $R_6$, $R_7$, $R_8$, $R_9$, $R_{10}$ and $R_{11}$ include, for example, methoxycarbonyl, ethoxycarbonyl, propoxycarbonyl, isopropoxycarbonyl, cyclopropoxycarbonyl, butoxycarbonyl, isobutoxycarbonyl, sec-butoxycarbonyl, tert-butoxycarbonyl, and the like. Preferred alkoxycarbonyl groups include methoxycarbonyl, ethoxycarbonyl, propoxycarbonyl, isopropoxycarbonyl and cyclopropoxycarbonyl.

Illustrative alkyl groups that may be used in $R_1$, $R_2$, $R_3$, $R_4$, $R_5$, $R_6$, $R_7$, $R_8$, $R_9$, $R_{10}$ and $R_{11}$ include, for example, methyl, ethyl, n-propyl, isopropyl, n-butyl, isobutyl, sec-butyl, tert-butyl, pentyl, isopentyl, neopentyl, tert-pentyl, 1-methylbutyl, 2-methylbutyl, 1,2-dimethylpropyl, hexyl, isohexyl, 1-methylpentyl, 2-methylpentyl, 3-methylpentyl, 1,1-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, cyclopropyl, cyclobutyl, cyclopentyl, cyclohexyl, cyclopropylmethyl, cyclopropylethyl, cyclobutylmethyl, and the like. Preferred alkyl groups include methyl, ethyl, n-propyl, isopropyl and cyclopropyl.

Illustrative amine groups that may be used in $R_1$, $R_2$, $R_3$, $R_4$, $R_5$, $R_6$, $R_7$, $R_8$, $R_9$, $R_{10}$ and $R_{11}$ include, for example, methylamine, dimethylamine, ethylamine, diethylamine, propylamine, dipropylamine, isopropylamine, diisopropylamine, butylamine, dibutylamine, tert-butylamine, di(tert-butyl)amine, ethylmethylamine, butylmethylamine, cyclohexylamine, dicyclohexylamine, and the like. Preferred amine groups include dimethylamine, diethylamine and diisopropylamine.

Illustrative silyl groups that may be used in $R_1$, $R_2$, $R_3$, $R_4$, $R_5$, $R_6$, $R_7$, $R_8$, $R_9$, $R_{10}$ and $R_{11}$ include, for example, silyl, trimethylsilyl, triethylsilyl, tris(trimethylsilyl)methyl, trisilylmethyl, methylsilyl and the like. Preferred silyl groups include silyl, trimethylsilyl and triethylsilyl.

Illustrative organometallic compounds of this invention include, for example, cyclopentadienylpyrrolylruthenium, methylcyclopentadienylpyrrolylruthenium, ethylcyclopentadienylpyrrolylruthenium, isopropylcyclopentadienylpyrrolylruthenium, tert-butylcyclopentadienylpyrrolylruthenium, methylcyclopentadienyl-2,5-dimethylpyrrolylruthenium, ethylcyclopentadienyl-2,5-dimethylpyrrolylruthenium, isopropylcyclopentadienyl-2,5-dimethylpyrrolylruthenium, tert-butylcyclopentadienyl-2,5-dimethylpyrrolylruthenium, methylcyclopentadienyltetramethylpyrrolylruthenium, ethylcyclopentadienyltetramethylpyrrolylruthenium, isopropylcyclopentadienyltetramethylpyrrolylruthenium, tert-butylcyclopentadienyltetramethylpyrrolylruthenium, 1,2-dimethylcyclopentadienylpyrrolylruthenium, 1,3-dimethylcyclopentadienylpyrrolylruthenium, 1,3-dimethylcyclopentadienyl-2,5-dimethylpyrrolylruthenium, 1,3-dimethylcyclopentadienyltetramethylpyrrolylruthenium, pentadienylpyrrolylruthenium, 2,4-dimethylpentadienylpyrrolylruthenium, 2,4-dimethylpentadienyl-2,5-dimethylpyrrolylruthenium, 2,4-dimethylpentadienyltetramethylpyrrolylruthenium, cyclohexadienylpyrrolylruthenium, cyclohexadienyl-2,5-dimethylpyrrolylruthenium, cyclohexadienyltetramethylpyrrolylruthenium, cycloheptadienylpyrrolylruthenium, cycloheptadienyl-2,5-dimethylpyrrolylruthenium, cycloheptadienyltetramethylpyrrolylruthenium, bis(pyrrolyl)ruthenium, 2,5-dimethylpyrrolylpyrrolylruthenium, tetramethylpyrrolylpyrrolylruthenium, bis(2,5-dimethylpyrrolyl)ruthenium, 2,5-dimethylpyrrolyltetramethylpyrrolylruthenium, and the like.

With respect to the claimed organometallic compounds of this invention, the following limitations apply: (i) when L and L' are both fully substituted pyrrolyl groups, then at least one of the pyrrolyl group substituents is other than methyl; (ii) when L and L' are both substituted indolyl groups, then at least one of the indolyl group substituents is other than hydrogen or methyl; (iii) when L is an unsubstituted cyclooctane group and L' is a substituted pyrrolyl group, then at least one of the pyrrolyl group substituents is other than methyl; (iv) when L is an unsubstituted cyclooctane group and L' is a substituted indolyl group, then at least one of the indolyl group substituents is other than hydrogen or methyl; and (v) when L is a substituted cyclohexadiene group and L' is a substituted pyrrolyl group, then at least one of the pyrrolyl group substituents is other than methyl.

As also indicated above, this invention also relates in part to a process for the production of an organometallic compound represented by the formula LML' wherein M is a metal or metalloid, L is a substituted or unsubstituted cyclopentadienyl group, a substituted or unsubstituted cyclopentadienyl-like group, a substituted or unsubstituted pentadienyl group, a substituted or unsubstituted pentadienyl-like group, a substituted or unsubstituted pyrrolyl group or a substituted or unsubstituted pyrrolyl-like group, and L' is a substituted or unsubstituted pyrrolyl group or a substituted or unsubstituted pyrrolyl-like group, which process comprises (i) reacting a metal source compound selected from a substituted or unsubstituted cyclopentadienyl halide metal, e.g., ruthenium, compound, a substituted or unsubstituted cyclopentadienyl-like halide metal, e.g., ruthenium, compound, a substituted or unsubstituted pentadienyl halide metal, e.g., ruthenium, compound, a substituted or unsubstituted pentadienyl-like halide metal, e.g., ruthenium, compound, a substituted or unsubstituted pyrrolyl halide metal, e.g., ruthenium, compound or a substituted or unsubstituted pyrrolyl-like halide metal, e.g., ruthenium, compound, with a base material in the presence of a solvent and under reaction conditions sufficient to produce a reaction mixture comprising said organometallic compound, and (ii) separating said organometallic compound from said reaction mixture. The organometallic compound yield resulting from the process of this invention can be 60% or greater, preferably 75% or greater, and more preferably 90% or greater.

The process is particularly well-suited for large scale production since it can be conducted using the same equipment, some of the same reagents and process parameters that can easily be adapted to manufacture a wide range of products. The process provides for the synthesis of organometallic precursor compounds using a process where all manipulations can be carried out in a single vessel, and which route to the organometallic precursor compounds does not require the isolation of an intermediate complex.

The metal source compound starting material may be selected from a wide variety of compounds known in the art. The invention herein most prefers metals selected from Ti, Zr, Hf, V, Nb, Ta, Cr, Mo, W, Mn, Tc, Re, Fe, Ru, Os, Co, Rh, Ir, Ni, Pd, Pt, Cu, Ag, Au, Zn, Cd, Hg, Al, Ga, Si, Ge, a Lanthanide series element or an Actinide series element. Illustrative metal source compounds include, for example, chlorobis(triphenylphosphine)(ethylcyclopentadienyl)ruthenium, bromobis(triphenylphosphine)(ethylcyclopentadienyl)ruthenium, chlorobis(triisopropylphosphite)(ethylcyclopentadienyl)ruthenium, chlorobis(triethylphosphine)(ethylcyclopentadienyl)ruthenium, chlorobis(triphenylphosphine)(cyclopentadienyl)ruthenium, chlorobis(triphenylphosphine)(methylcyclopentadienyl)ruthenium, chlorobis(triphenylphosphine)(2,4-dimethylpentadienyl)ruthenium, chlorobis(triphenylphosphine)(pyrrolyl)ruthenium, chlorobis(triphenylphosphine)(2,5-dimethylpyrrolyl)ruthenium, chlorobis(triphenylphosphine)(tetramethylpyrrolyl)ruthenium, and the like.

The process of the invention is preferably useful in generating organometallic ruthenium compounds that have varied chemical structures and physical properties. A wide variety of reaction materials may be employed in the processes of this invention. For example, in the preparation of the metal source compounds, ruthenium starting materials that may be used include commercial grade Ru(III) chloride hydrate, α-ruthenium(III) chloride, β-ruthenium(III) chloride, ruthenium(III) nitrate, $(PPh_3)_xRuCl_2$ (x=3-4) and the like.

The concentration of the metal source compound starting material can vary over a wide range, and need only be that minimum amount necessary to react with the base compound and to provide the given metal concentration desired to be employed and which will furnish the basis for at least the amount of metal necessary for the organometallic compounds of this invention. In general, depending on the size of the reaction mixture, metal source compound starting material concentrations in the range of from about 1 millimole or less to about 10,000 millimoles or greater, should be sufficient for most processes.

The base starting material may be selected from a wide variety of compounds known in the art. Illustrative bases include any base with a pKa greater than about 10, preferably greater than about 20, and more preferably greater than about 25. The base material is preferably lithium pyrrolides, lithium pentadienides, lithium cyclopentadienides, sodium pyrrolides, sodium pentadienides, sodium cyclopentadienides, bromomagnesium pyrrolides, bromomagnesium pentadienides, bromomagnesium cyclopentadienides, and the like.

The concentration of the base starting material can vary over a wide range, and need only be that minimum amount necessary to react with the metal source compound starting material. In general, depending on the size of the first reaction mixture, base starting material concentrations in the range of from about 1 millimole or less to about 10,000 millimoles or greater, should be sufficient for most processes.

The solvent employed in the method of this invention may be any saturated and unsaturated hydrocarbons, aromatic hydrocarbons, aromatic heterocycles, alkyl halides, silylated hydrocarbons, ethers, polyethers, thioethers, esters, thioesters, lactones, amides, amines, polyamines, nitriles, silicone oils, other aprotic solvents, or mixtures of one or more of the above; more preferably, diethylether, pentanes, or dimethoxyethanes; and most preferably hexanes or THF. Any suitable solvent which does not unduly adversely interfere with the intended reaction can be employed. Mixtures of one or more different solvents may be employed if desired. The amount of solvent employed is not critical to the subject invention and need only be that amount sufficient to solubilize the reaction components in the reaction mixture. In general, the amount of solvent may range from about 5 percent by weight up to about 99 percent by weight or more based on the total weight of the reaction mixture starting materials.

Reaction conditions for the reaction of the base compound with the metal source compound, such as temperature, pressure and contact time, may also vary greatly and any suitable combination of such conditions may be employed herein. The reaction temperature may be the reflux temperature of any of the aforementioned solvents, and more preferably between about −80° C. to about 150° C., and most preferably between about 20° C. to about 80° C. Normally the reaction is carried out under ambient pressure and the contact time may vary from a matter of seconds or minutes to a few hours or greater. The reactants can be added to the reaction mixture or combined in any order. The stir time employed can range from about 0.1 to about 400 hours, preferably from about 1 to 75 hours, and more preferably from about 4 to 16 hours, for all steps.

Other alternative processes that may be used in preparing the organometallic ruthenium compounds of this invention include those disclosed in U.S. Pat. No. 6,605,735 B2 and U.S. Patent Application Publication No. US 2004/0127732 A1, published Jul. 1, 2004, the disclosure of which is incorporated herein by reference. The organometallic compounds of this invention may also be prepared by conventional processes such as described in Legzdins, P. et al. Inorg. Synth. 1990, 28, 196 and references therein.

For organometallic compounds prepared by the method of this invention, purification can occur through recrystallization, more preferably through extraction of reaction residue (e.g., hexane) and chromatography, and most preferably through sublimation and distillation.

Those skilled in the art will recognize that numerous changes may be made to the method described in detail herein, without departing in scope or spirit from the present invention as more particularly defined in the claims below.

Examples of techniques that can be employed to characterize the organometallic compounds formed by the synthetic methods described above include, but are not limited to, analytical gas chromatography, nuclear magnetic resonance, thermogravimetric analysis, inductively coupled plasma mass spectrometry, differential scanning calorimetry, vapor pressure and viscosity measurements.

Relative vapor pressures, or relative volatility, of organometallic compound precursors described above can be measured by thermogravimetric analysis techniques known in the art. Equilibrium vapor pressures also can be measured, for example by evacuating all gases from a sealed vessel, after which vapors of the compounds are introduced to the vessel and the pressure is measured as known in the art.

The organometallic compound precursors described herein are preferably liquid at room temperature, i.e., 20° C., hydrogen reducible, deposit in a self-limiting manner, and are well suited for preparing in-situ powders and coatings. For instance, a liquid organometallic compound precursor can be applied to a substrate and then heated to a temperature sufficient to decompose the precursor, thereby forming a metal or metal oxide coating on the substrate. Applying a liquid precursor to the substrate can be by painting, spraying, dipping or by other techniques known in the art. Heating can be conducted in an oven, with a heat gun, by electrically heating the substrate, or by other means, as known in the art. A layered coating can be obtained by applying an organometallic compound precursor, and heating and decomposing it, thereby forming a first layer, followed by at least one other coating with the same or different precursors, and heating.

Liquid organometallic compound precursors such as described above also can be atomized and sprayed onto a substrate. Atomization and spraying means, such as nozzles, nebulizers and others, that can be employed are known in the art.

In preferred embodiments of the invention, an organometallic compound, such as described above, is employed in gas phase deposition techniques for forming powders, films or coatings. The compound can be employed as a single source precursor or can be used together with one or more other precursors, for instance, with vapor generated by heating at least one other organometallic compound or metal complex. More than one organometallic compound precursor, such as described above, also can be employed in a given process.

As indicated above, this invention relates in part to organometallic mixtures comprising (i) a first organometallic compound represented by the formula LML' wherein M is a transition metal, L is a substituted or unsubstituted cyclopentadienyl group, a substituted or unsubstituted cyclopentadienyl-like group, a substituted or unsubstituted pentadienyl group, a substituted or unsubstituted pentadienyl-like group, a substituted or unsubstituted pyrrolyl group or a substituted or unsubstituted pyrrolyl-like group, and L' is a substituted or unsubstituted pyrrolyl group or a substituted or unsubstituted pyrrolyl-like group and (ii) one or more different organometallic compounds (e.g., a hafnium-containing, tantalum-containing or molybdenum-containing organometallic precursor compound).

Deposition can be conducted in the presence of other gas phase components. In an embodiment of the invention, film deposition is conducted in the presence of at least one non-reactive carrier gas. Examples of non-reactive gases include inert gases, e.g., nitrogen, argon, helium, as well as other gases that do not react with the organometallic compound precursor under process conditions. In other embodiments, film deposition is conducted in the presence of at least one reactive gas. Some of the reactive gases that can be employed include but are not limited to hydrazine, oxygen, hydrogen, air, oxygen-enriched air, ozone ($O_3$), nitrous oxide ($N_2O$), water vapor, organic vapors, ammonia and others. As known in the art, the presence of an oxidizing gas, such as, for example, air, oxygen, oxygen-enriched air, $O_3$, $N_2O$ or a vapor of an oxidizing organic compound, favors the formation of a metal oxide film.

In an embodiment, hydrogen or another reducing gas may be used in a BEOL atomic layer deposition process at temperatures below 300° C. so that the deposition can be carried out in a manner compatible with the rest of the BEOL integration strategy. An illustrative atomic layer deposition strategy for forming BEOL interconnects using ruthenium is as follows: low K repair, tantalum nitride atomic layer deposition, ruthenium atomic layer deposition and copper electrochemical deposition. Hydrogen reducible ruthenium complexes may also be used for the integration of ruthenium in MIM stacked cell DRAM capacitors.

In addition to being hydrogen reducible, the ruthenium complexes of this invention deposit in a self-limiting manner. For example, in the absence of a reactant gas, the substrate becomes saturated with a monolayer, or fraction of a monolayer, of the dissociatively chemisorbed ruthenium precursor. In a self-limiting deposition, only one layer of organometallic precursor is deposited at a time. Pyrrolyl-containing ruthenium precursors deposited in a self-limiting manner by atomic layer deposition may enable conformal film growth over high aspect ratio trench architectures in a reducing environment.

As indicated above, this invention also relates in part to a method for producing a film, coating or powder. The method includes the step of decomposing at least one organometallic compound precursor, thereby producing the film, coating or powder, as further described below.

Deposition methods described herein can be conducted to form a film, powder or coating that includes a single metal or a film, powder or coating that includes a single metal oxide. Mixed films, powders or coatings also can be deposited, for instance mixed metal oxide films. A mixed metal oxide film can be formed, for example, by employing several organometallic precursors, at least one of which being selected from the organometallic compounds described above.

Gas phase film deposition can be conducted to form film layers of a desired thickness, for example, in the range of from about 1 nm to over 1 mm. The precursors described herein are particularly useful for producing thin films, e.g., films having a thickness in the range of from about 10 nm to about 100 nm. Films of this invention, for instance, can be considered for fabricating metal electrodes, in particular as n-channel metal electrodes in logic, as capacitor electrodes for DRAM applications, and as dielectric materials.

The method also is suited for preparing layered films, wherein at least two of the layers differ in phase or composition. Examples of layered film include metal-insulator-semiconductor, and metal-insulator-metal.

In an embodiment, the invention is directed to a method that includes the step of decomposing vapor of an organometallic compound precursor described above, thermally, chemically, photochemically or by plasma activation, thereby forming a film on a substrate. For instance, vapor generated by the compound is contacted with a substrate having a temperature sufficient to cause the organometallic compound to decompose and form a film on the substrate.

The organometallic compound precursors can be employed in chemical vapor deposition or, more specifically, in metalorganic chemical vapor deposition processes known in the art. For instance, the organometallic compound precursors described above can be used in atmospheric, as well as in low pressure, chemical vapor deposition processes. The compounds can be employed in hot wall chemical vapor deposition, a method in which the entire reaction chamber is heated, as well as in cold or warm wall type chemical vapor deposition, a technique in which only the substrate is being heated.

The organometallic compound precursors described above also can be used in plasma or photo-assisted chemical vapor deposition processes, in which the energy from a plasma or electromagnetic energy, respectively, is used to activate the chemical vapor deposition precursor. The compounds also can be employed in ion-beam, electron-beam assisted chemical vapor deposition processes in which, respectively, an ion beam or electron beam is directed to the substrate to supply energy for decomposing a chemical vapor deposition precursor. Laser-assisted chemical vapor deposition processes, in which laser light is directed to the substrate to affect photolytic reactions of the chemical vapor deposition precursor, also can be used.

The method of the invention can be conducted in various chemical vapor deposition reactors, such as, for instance, hot or cold-wall reactors, plasma-assisted, beam-assisted or laser-assisted reactors, as known in the art.

Examples of substrates that can be coated employing the method of the invention include solid substrates such as metal substrates, e.g., Al, Ni, Ti, Co, Pt, Ta; metal silicides, e.g., $TiSi_2$, $CoSi_2$, $NiSi_2$; semiconductor materials, e.g., Si, SiGe, GaAs, InP, diamond, GaN, SiC; insulators, e.g., $SiO_2$, $Si_3N_4$, $HfO_2$, $Ta_2O_5$, $Al_2O_3$, barium strontium titanate (BST); barrier materials, e.g., TiN, TaN; or on substrates that include combinations of materials. In addition, films or coatings can be formed on glass, ceramics, plastics, thermoset polymeric materials, and on other coatings or film layers. In preferred embodiments, film deposition is on a substrate used in the manufacture or processing of electronic components. In other embodiments, a substrate is employed to support a low resistivity conductor deposit that is stable in the presence of an oxidizer at high temperature or an optically transmitting film.

The method of this invention can be conducted to deposit a film on a substrate that has a smooth, flat surface. In an embodiment, the method is conducted to deposit a film on a substrate used in wafer manufacturing or processing. For instance, the method can be conducted to deposit a film on patterned substrates that include features such as trenches, holes or vias. Furthermore, the method of the invention also can be integrated with other steps in wafer manufacturing or processing, e.g., masking, etching and others.

Chemical vapor deposition films can be deposited to a desired thickness. For example, films formed can be less than 1 micron thick, preferably less than 500 nanometers and more preferably less than 200 nanometers thick. Films that are less than 50 nanometers thick, for instance, films that have a thickness between about 0.1 and about 20 nanometers, also can be produced.

Organometallic compound precursors described above also can be employed in the method of the invention to form films by atomic layer deposition (ALD) or atomic layer nucleation (ALN) techniques, during which a substrate is exposed to alternate pulses of precursor, oxidizer and inert gas streams. Sequential layer deposition techniques are described, for example, in U.S. Pat. Nos. 6,287,965 and in 6,342,277. The disclosures of both patents are incorporated herein by reference in their entirety.

For example, in one ALD cycle, a substrate is exposed, in step-wise manner, to: a) an inert gas; b) inert gas carrying precursor vapor; c) inert gas; and d) oxidizer, alone or together with inert gas. In general, each step can be as short as the equipment will permit (e.g. milliseconds) and as long as the process requires (e.g. several seconds or minutes). The duration of one cycle can be as short as milliseconds and as long as minutes. The cycle is repeated over a period that can range from a few minutes to hours. Film produced can be a few nanometers thin or thicker, e.g., 1 millimeter (mm).

The method of the invention also can be conducted using supercritical fluids. Examples of film deposition methods that use supercritical fluid that are currently known in the art include chemical fluid deposition; supercritical fluid transport-chemical deposition; supercritical fluid chemical deposition; and supercritical immersion deposition.

Chemical fluid deposition processes, for example, are well suited for producing high purity films and for covering complex surfaces and filling of high-aspect-ratio features. Chemical fluid deposition is described, for instance, in U.S. Pat. No. 5,789,027. The use of supercritical fluids to form films also is described in U.S. Pat. No. 6,541,278 B2. The disclosures of these two patents are incorporated herein by reference in their entirety.

In an embodiment of the invention, a heated patterned substrate is exposed to one or more organometallic compound precursors, in the presence of a solvent, such as a near critical or supercritical fluid, e.g., near critical or supercritical $CO_2$. In the case of $CO_2$, the solvent fluid is provided at a pressure above about 1000 psig and a temperature of at least about 30° C.

The precursor is decomposed to form a metal film on the substrate. The reaction also generates organic material from the precursor. The organic material is solubilized by the solvent fluid and easily removed away from the substrate. Metal oxide films also can be formed, for example by using an oxidizing gas.

In an example, the deposition process is conducted in a reaction chamber that houses one or more substrates. The substrates are heated to the desired temperature by heating the entire chamber, for instance, by means of a furnace. Vapor of the organometallic compound can be produced, for example, by applying a vacuum to the chamber. For low boiling compounds, the chamber can be hot enough to cause vaporization of the compound. As the vapor contacts the heated substrate surface, it decomposes and forms a metal or metal oxide film. As described above, an organometallic compound precursor can be used alone or in combination with one or more components, such as, for example, other organometallic precursors, inert carrier gases or reactive gases.

In a system that can be used in producing films by the method of the invention, raw materials can be directed to a gas-blending manifold to produce process gas that is supplied to a deposition reactor, where film growth is conducted. Raw materials include, but are not limited to, carrier gases, reactive gases, purge gases, precursor, etch/clean gases, and others. Precise control of the process gas composition is accomplished using mass-flow controllers, valves, pressure transducers, and other means, as known in the art. An exhaust manifold can convey gas exiting the deposition reactor, as well as a bypass stream, to a vacuum pump. An abatement system, downstream of the vacuum pump, can be used to remove any hazardous materials from the exhaust gas. The deposition system can be equipped with in-situ analysis system, including a residual gas analyzer, which permits measurement of the process gas composition. A control and data acquisition system can monitor the various process parameters (e.g., temperature, pressure, flow rate, etc.).

The organometallic compound precursors described above can be employed to produce films that include a single metal or a film that includes a single metal oxide. Mixed films also can be deposited, for instance mixed metal oxide films. Such films are produced, for example, by employing several organometallic precursors. Metal films also can be formed, for example, by using no carrier gas, vapor or other sources of oxygen.

Films formed by the methods described herein can be characterized by techniques known in the art, for instance, by X-ray diffraction, Auger spectroscopy, X-ray photoelectron emission spectroscopy, atomic force microscopy, scanning electron microscopy, and other techniques known in the art. Resistivity and thermal stability of the films also can be measured, by methods known in the art.

In addition to their use in semiconductor applications as chemical vapor or atomic layer deposition precursors for film depositions, the organometallic compounds of this invention may also be useful, for example, as catalysts, fuel additives and in organic syntheses.

Various modifications and variations of this invention will be obvious to a worker skilled in the art and it is to be understood that such modifications and variations are to be included within the purview of this application and the spirit and scope of the claims.

EXAMPLE 1

A dry 500 milliliter 3-neck round-bottom flask was equipped with a condenser (with at flow through adaptor at the top) and charged with a stir bar. The flask was clamped in a fume hood resting on a heating mantle (attached to a variac) above a stir plate. To the flask was added chlorobis (triphenylphosphine)-(ethylcyclopentadienyl)ruthenium (14.8 grams, 0.020 mol), and the system was purged with nitrogen for 15 minutes. After purging the flask was capped with a glass stopper and a septum, and a slow nitrogen flow was established through the t adaptor on top of the condenser vented to an oil bubbler. Via cannula, anhydrous toluene (150 milliliters) was added and stirring commenced. A THF (50 milliliters) solution of lithium pyrrolide (1.6 grams, 0.022 mol) was transferred to the toluene suspension via cannula. The brown solution was heated to gentle reflux and stirred for 16 hours. After cooling to room temperature, the solvent was removed under reduced pressure. The resulting residue was agitated in hexanes (4×100 milliliters) and filtered through a medium porosity frit. The hexanes were removed from the yellow filtrate under reduced pressure, and the resulting dark yellow liquid was vacuum distilled (approximately 0.3 torr) through a short path distillation head. Product collection occurred at approximately 100° C. The yellow liquid collected was characterized by NMR and GC-MS. MS (M+, relative intensity): 260 (100), 246 (40), 193 (33), 167 (9). $^1$H NMR (300 MHz, toluene-$d_8$, δ): 5.64 (t, α-pyrrolyl, J=1 Hz), 4.62 (t, β-pyrrolyl, J=1 Hz), 4.38 (t, Cp, J=2 Hz), 4.30 (t, Cp, J=2 Hz), 2.04 (q, $CH_2$, J=8), 1.02 (t, $CH_3$, J=8). The product is ethylcyclopentadienylpyrrolylruthenium represented by the structure below.

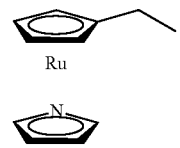

EXAMPLE 2

Lithium 2,5-dimethylpyrrolide was synthesized separately by standard lithiation techniques utilizing n-butyllithium and 2,5-dimethylpyrrole in hexanes. Within a dry nitrogen atmosphere glove box a dry, one-neck 1 liter round-bottom flask with an airfree Teflon valve was charged with a stir bar. To the flask was added lithium 2,5-dimethylpyrrolide (6.0 grams, 0.059 mol), anhydrous THF (75 milliliters) and anhydrous hexanes (300 milliliters). Tris(triphenylphosphine)-dichlororuthenium (14.3 grams, 0.015 mol) was added. The flask was capped, removed from the glove box, fitted with a condenser under a nitrogen purge, and refluxed under nitrogen (with stirring) in a fume hood (14 hours). After cooling to room temperature, the solvent was removed under reduced pressure, and the residue was returned to the glove box. The crude material was agitated with hexanes, then filtered through a medium porosity frit. The filtrate was reduced to about 10 milliliters, then loaded on to a silica gel column. Elution with anhydrous diethylether removed the remaining triphenylphosphine. Elution with anhydrous THF produced a bright yellow band, which was collected, and the THF was removed to yield a light yellow/beige solid. The pure compound, bis(2,5-dimethylpyrrolyl)ruthenium, was thermally stable in a dry nitrogen atmosphere. GC/MS (M+, relative intensity): 289 (100), 193 (26). $^1$H NMR (300 MHz, $C_6D_6$, δ): 4.45 (s, β-pyrrolyl, 2H), 2.11 (s, $CH_3$, 6H). DSC: mp=73° C.

The invention claimed is:

1. A method for producing a film, coating or powder by decomposing an organometallic compound represented by the formula LML' wherein M is ruthenium, L is a substituted or unsubstituted cyclopentadienyl group, and L' is an unsubstituted pyrrolyl group, wherein said organometallic compound is a liquid at 20° C. and atmospheric pressure thereby producing the film, coating or powder.

2. The method of claim 1 wherein the decomposing of said organometallic compound is thermal, chemical, photochemical or plasma-activated.

3. The method of claim 2 wherein said organometallic compound is vaporized and the vapor is directed into a deposition reactor housing a substrate.

4. The method of claim 3 wherein said substrate is comprised of a material selected from the group consisting of a metal, a metal silicide, a semiconductor, an insulator and a barrier material.

5. The method of claim 1 wherein said substrate is a patterned wafer.

6. The method of claim 1 wherein said film, coating or powder is produced by a gas phase deposition.

* * * * *